United States Patent [19]

Eiden et al.

[11] Patent Number: 4,859,664
[45] Date of Patent: Aug. 22, 1989

[54] DERIVATIVES OF 2,3,4,5,6,7-HEXAHYDRO-2,7-METHANO-1,5-BENZOXAZONINES AND -1,4-BENZOXAZONINES, PROCESSES FOR THEIR PRODUCTION AND THEIR USE AS PHARMACEUTICALS

[75] Inventors: Friedrich Eiden, Gräfeling; Peter Gmeiner; Jürgen Schünemann, both of Munich, all of Fed. Rep. of Germany

[73] Assignee: Madaus GmbH & Company, Cologne, Fed. Rep. of Germany

[21] Appl. No.: 93,553

[22] Filed: Sep. 4, 1987

[30] Foreign Application Priority Data

Sep. 8, 1986 [DE] Fed. Rep. of Germany ....... 3630539

[51] Int. Cl.$^4$ .................... C07D 267/00; A61K 31/33
[52] U.S. Cl. .................................. 514/217; 514/454; 540/581; 549/386
[58] Field of Search ................. 540/468, 581; 549/386; 514/217, 454

[56] References Cited

U.S. PATENT DOCUMENTS

| | | | |
|---|---|---|---|
| 3,441,564 | 4/1969 | Krapcho et al. | 540/468 |
| 3,446,820 | 5/1969 | Klohs et al. | 540/468 |
| 4,100,277 | 7/1978 | Demerson et al. | 540/468 |

Primary Examiner—Mary C. Lee
Assistant Examiner—Zinna Northington
Attorney, Agent, or Firm—Felfe & Lynch

[57] ABSTRACT

New 2,3,4,5,6,7-hexahydro-2,7-methano-1,5-benzoxazonine and -1,4-benzoxazonine compounds of the formula

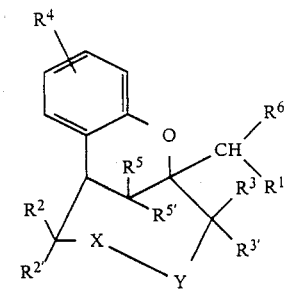

have useful pharmaceutical properites. They are prepared from ketones of the formula

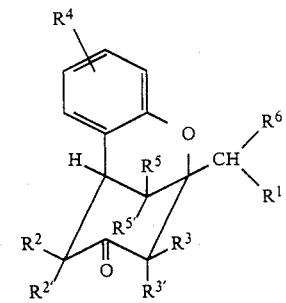

via a lactone intermediate. In the formula, the various R substitutes are generally hydrogen or alkyl, with $R^4$ also being halogen or alkoxy and $R^3/R^{3'}$ also being phenyl. $R^1$ may be joined with $R^5/R^{5'}$ in a 5- to 7-membered ring possibly interrupted by O, S, SO$_2$ or amino. One of X and Y is CH$_2$; the other is amino. The starting ketones also have pharmaceutical properties. The lactone intermediates are new compounds.

15 Claims, No Drawings

DERIVATIVES OF 2,3,4,5,6,7-HEXAHYDRO-2,7-METHANO-1,5-BENZOXAZONINES AND -1,4-BENZOXAZONINES, PROCESSES FOR THEIR PRODUCTION AND THEIR USE AS PHARMACEUTICALS

The present invention is concerned with new 2,3,4,5,6,7-hexahydro-2,7-methano-1,5-benzoxazonine and -1,4-benzoxazonine compounds, with processes for the preparation thereof and with pharmaceutical compositions containing them.

In recent years, numerous compounds have been synthesized with the object of developing effective analgesics which do not possess the side effects of known analgesics. In this regard, special mention is to be made of the compounds with a morphine-like structure, as well as salicylic acid derivatives.

Compounds with a morphine-like structure, for example substituted pyridinecarboxylic acid derivatives, possess addiction-producing properties (see A. M. Washton, R. B. Resnick and R. A. Rawson, 1979, Proceedings of the 41st Annual Scientific Meeting of the Committee on Problems of Drug Dependence, NIDA Res. Monogr. GPO, in the press; D. R. Jasinski, W. R. Martin and R. Hoeldtke, Clin. Pharmacol. Ther., 11, 385–403/1979 and D. R. Jasinski, W. R. Martin and R. Hoeldtke, Clin. Pharmacol. Ther., 12, 613–649/1971). However, various analgesics prepared synthetically and, in some cases, differing distinctly from the structure of morphine, possess these properties to a more or less marked extent.

Salicylic acid derivatives display poor gastrointestinal compatibility and, in the case of prolonged use, result in kidney damage (see E. Arrigoni-Martelli, Inflammation and Antiinflammatories, pub. Spectrum, New York, 343 et seq., 1977; P. L. Boardman and E. D. Hart, Clinical Measurement of the antiinflammatory effects of salicylates in rheumatoid arthritis, B.M.J., 4, 264–268/1967; and H. E. Paulus and M. W. Whitehouse, Nonsteroid antiinflammatory agents, Ann. Rev. Pharmacol., 13, 107–125/1973).

European Patent Specification No. 80302724.2 describes compounds with an effect on the central nervous system of the general formula:

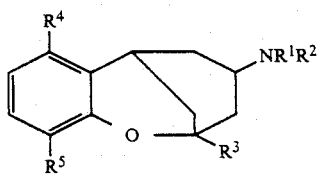

Federal Republic of Germany Patent Specification No. 24 22 309 describes 2,3,4,5,6,7-hexahydro-1,6-methano-1H-4-benzazonine derivatives which are analgesics, anti-tussives and sedatives. However, both classes of compounds have only a remote structural similarity with the compounds according to the present invention.

Surprisingly, we have found that compounds of the following general formula (I) are strongly effective analgesics with only slight side effects and without addiction-producing properties.

Thus, according to the present invention, there are provided compounds of the general formula:

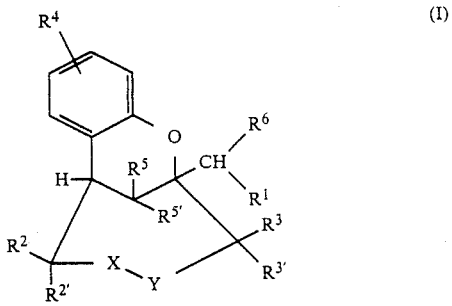

wherein $R^1$ is a hydrogen atom or a $C_1$–$C_4$ alkyl radical or $R^1$, together with $R^5$ or $R^{5'}$, can form an additional five-, six- or seven-membered ring and stand for —$(CH_2)_n$— or for —$(CH_2)_m$—Z—$(CH_2)_o$—, n being 2, 3 or 4 and m and o being 0, 1, 2 or 3, m+o being 1, 2 or 3 and Z is an oxygen or sulphur atom or an $SO_2$ or $NR^{10}$ radical, $R^{10}$ being a hydrogen atom, a $C_1$–$C_4$-alkyl radical or a $C_2$–$C_5$-acyl radical, $R^2$ and $R^{2'}$ are hydrogen atoms or $C_1$–$C_4$-alkyl radicals, at least one of them being a hydrogen atom, $R^3$ and $R^{3'}$ are hydrogen atoms, $C_1$–$C_4$-alkyl radicals or phenyl radicals, at least one of them being a hydrogen atom, $R^4$ is a hydrogen or halogen atom (chlorine or bromine), a hydroxyl group or a $C_1$–$C_2$-alkoxy or $C_1$–$C_4$-alkyl radical, the substituent being in the ortho- or para-position to the oxygen atom, $R^5$ and $R^{5'}$ are hydrogen atoms or $C_1$–$C_4$-alkyl radicals or form with $R^1$ a ring as defined above, $R^6$ is a hydrogen atom or a $C_1$–$C_4$-alkyl radical and X is $NR^7$ and Y is $CH_2$ or X is $CH_2$ and Y is $NR^7$, $R^7$ being a hydrogen atom or a $C_1$–$C_4$-alkyl radical; and the pharmaceutically acceptable acid-addition salts thereof.

According to the present invention, the $C_1$–$C_4$-alkyl radicals and the $C_2$–$C_5$-acyl radicals can be straight-chained or branched. The $C_1$–$C_4$-alkyl radical is preferably a methyl, ethyl or isopropyl radical, the methyl radical being especially preferred.

When $R^1$, together with $R^5$ or $R^{5'}$, forms a ring, it preferably stands for —$(CH_2)_n$—, n especially preferably being 3.

Compounds of general formula (I) readily form salts with a good physiological compatibility. Such salts are formed, for example, with inorganic acids, such as hydrochloric acid, hydrobromic acid and sulphuric acid, as well as with organic acids, such as acetic acid, tartaric acid, dibenzoyltartaric acid, citric acid, malic acid and fumaric acid.

Compounds of general formula (I) are usually present as racemates but can be resolved into the optical antipodes and used as the pure optical antipodes.

Compounds of general formula (I) and derivatives thereof have hitherto not been described in the literature. They thus represent a novel type of structure with unusually favourable pharmacological properties.

Of the compounds of general formula (I), the regioisomers with the nitrogen atom in the 5-position possess a strong effectiveness. Especially effective compounds of this subgroup are represented by the general formula:

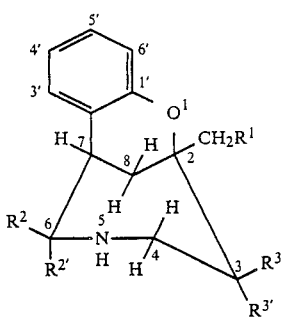

wherein $R^1$ is a hydrogen atom or a $C_1$–$C_4$-alkyl radical, $R^2$ and $R^{2'}$ are hydrogen atoms or $C_1$–$C_4$-alkyl radicals, at least one of which is a hydrogen atom, and $R^3$ and $R^{3'}$ are hydrogen atoms, $C_1$–$C_4$-alkyl radicals or phenyl radicals, at least one of which is a hydrogen atom.

Examples of this subgroup includes 2,3,4,5,6,7-hexahydro-2-methyl-2,7-methanol-1,5-benzoxazonine (IA; $R^1$, $R^2$, $R^{2'}$, $R^3$ and $R^{3'}$ are all hydrogen atoms) and 2,3,4,5,6,7-hexahydro-2,6-dimethyl-2,7-methanol-1,5-benzoxazonine (IA; $R^2$ is a methyl radical and $R^1$, $R^{2'}$, $R^3$ and $R^{3'}$ are all hydrogen atoms).

Amongst the compounds of general formula (I) which have an additional ring between $R^1$ and $R^5$ or $R^1$ and $R^{5'}$, the subgroup of the following general formula is of especial importance:

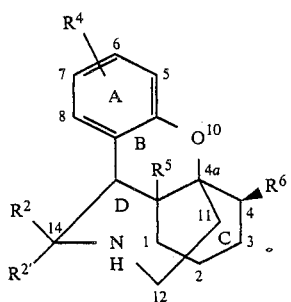

wherein $R^2$ and $R^{2'}$ are hydrogen atoms or $C_1$–$C_4$-alkyl radicals, at least one of which is a hydrogen atom, $R^4$ is a hydrogen, chlorin or bromine atom, a $C_1$–$C_2$-alkoxy radical, a $C_1$–$C_4$-alkyl radical or a hydroxyl group, the substituent being in the ortho- or para-position to the oxygen atom, $R^5$ is a hydrogen atom or a $C_1$–$C_4$-alkyl radical and $R^6$ is a hydrogen atom or a $C_1$–$C_4$-alkyl radical.

As an example thereof, there is mentioned B/C-trans-1,2,3,4,4a,9a-hexahydro-4-methyl-4a,9-(3-azabutano)-xanthene (IB: $R^6$ is a methyl radical and $R^2$, $R^{2'}$, $R^4$ and $R^5$ are all hydrogen atoms).

Of especial importance for the effectiveness of the compounds of general formula (I) is the mutual spatial arrangement of a hexahydroazepine ring to a dihydrobenzopyran ring system. The special relative position of these ring systems to one another is also responsible for the strong effectiveness of the compounds of general formula (IA) and (IB).

The compounds of general formula (I), in which $R^7$ is a hydrogen atom, can be prepared by starting from the corresponding lactams of general formula (I) but in which X is NH and Y is CO or X is CO and Y is NH, whereas the other substituents have the same meanings as given above. Compounds of general formula (I), in which $R^7$ is a hydrogen atom can be obtained from these lactams by reduction. For the reduction of the lactams, there can be used complex hydrides, boran, catalytic hydrogenation and other known processes. It is especially favourable to use lithium aluminium hydride as reducing agent in an inert solvent, for example diethyl ether, dioxan or tetrahydrofuran. In the case of lactams which are not very reactive or those which could form complexes with lithium aluminium hydride, the addition of an activator, for example aluminium trichloride, to the reaction mixture has proved to be advantageous.

Compounds of general formula (I), in which $R^7$ is a $C_1$–$C_4$-alkyl radical, can, in the case of the methyl compound, preferably be obtained by N-methylation with the help of the Leuckart-Wallach reaction (formic acid/formaldehyde or other aldehydes) or, quite generally, with an alkylation agent $RX_1$ in the presence of a base. In this case, R is a $C_1$–$C_4$-alkyl radical and $X_1$ is a halogen atom, a sulphonate group or some other group which can readily be removed. Furthermore, the alkylation can be achieved by N-acylation and subsequent reduction, for example with lithium aluminium hydride.

The previously unknown lactams of general formula (I), in which X is NH and Y is CO or X is CO and Y is NH, are advantageously prepared from ketones of the general formula:

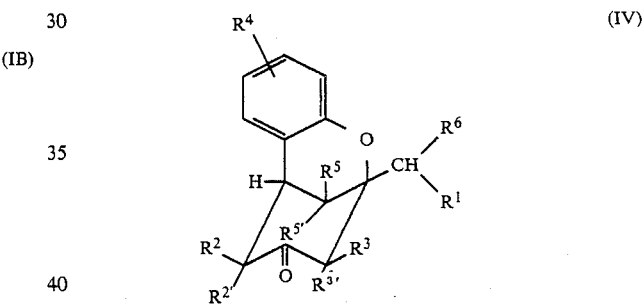

wherein $R^1$, $R^2$, $R^{2'}$, $R^3$, $R^{3'}$, $R^4$, $R^5$, $R^{5'}$ and $R^6$ have the meanings given above in connection with general formula (I).

For the conversion of ketones of general formula (IV) into lactams of general formula (I), in which X is NH and Y is CO or X is CO and Y is NH, it is especially preferred to use the Schmidt rearrangement with hydrazoic acid, as well as a conversion into the oxime and subsequent Beckmann rearrangement.

In the second case, the oxime is prepared by standard processes of organic chemistry this oxime being obtained as a syn/anti mixture. Some oximes have already been prepared for other purposes from compounds of general formula (IV) (see R. Kuhn and D. Weiser, Chem. Ber., 88, 1601/1955; as well as European Patent Application No. 80302723.2). The mixture of the syn- and anti-oximes can be converted into the lactam with the help of a Beckmann rearrangement. As catalysts for this purpose, there can be used, for example, phosphorus pentachloride, concentrated sulphuric acid, formic acid, triphenyl phosphorus/carbon tetrachloride and other reagents (see C. G. MacCarty in S. Patai "The Chemistry of the Carbon-Nitrogen Double Bond", pp. 405-439, Pub. Interscience, New York, 1970).

In the case of the Schmidt rearrangement, it is possible, in a one-step process, to convert the cyclic ketone of general formula (IV) into a lactam of general formula (I), in which X is NH and Y is CO or X is CO and Y is NH. For this purpose, there is used hydrazoic acid which is liberated from sodium azide with an acid. As additional catalyst for the reaction, there can be used concentrated sulphuric acid, concentrated hydrochloric acid, Lewis acids and other compounds (see, for example, A. L. J. Beckwith in J. Jabicki, "The Chemistry of the Amides", pp. 137-145, pub. Interscience, New York, 1970). The reaction is preferably carried out with sodium azide in glacial acetic acid in the presence of concentrated sulphuric acid.

When $R^2$, $R^{2'}$ is hydrogen, in the case of the Beckmann rearrangement, as well as in the case of the Schmidt reaction, two regioisomers of the lactam are obtained, wherein X is NH and Y is CO or X is CO and Y is NH in general formula (I). A separation of the isomers can be achieved by crystallisation, column chromatography, HPLC and other known separation processes. In this way, the regioisomers can be obtained in pure form. Alternatively, the mixture of the regioisomeric lactams can be directly subjected to a reduction to give amines of general formula (I), wherein $R^7$ is a hydrogen atom. A separation of the two regioisomers of general formula (I), wherein X is NH and Y is $CH_2$ and X is $CH_2$ and Y is NH, can also be achieved at the amine stage. For this purpose, it is possible to use fractional crystallisation or precipitation, column chromatography, HPLC and similar processes. When $R^2$ is an alkyl radical, there are only obtained the isomers with nitrogen in the 5-position (for example IA and IB) and the reaction then takes place regioselectively.

Some compounds of general formula (IV) and the preparation thereof are already known from the literature (see R. Kuhn and D. Weiser, Chem. Ber. 88, 1601/1955; European Patent Application No. 80302724.2; and F. Eiden and P. Gmeiner, Arch. Pharm., 319,431/1986). However, numerous compounds of general formula (IV) are unknown. They can be synthesised in the manner described hereinafter with a great breadth of variety according to a process which is, in principle, known. For this purpose, from a substituted salicylaldehyde and a methyl ketone, there is prepared the readily obtainable enones of general formula (V):

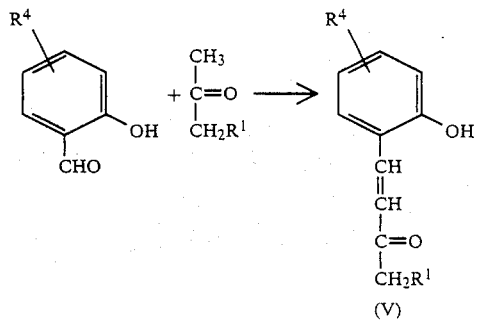

wherein $R^1$ is a hydrogen atom or a $C_1-C_4$-alkyl radical and $R^4$ is a hydrogen, chlorine or bromine atom, a $C_1-C_2$-alkoxy or $C_1-C_4$-alkyl radical or a hydroxyl group, the substituents being in the ortho- or para-position to the oxygen atom.

The condensation to give compounds of general formula (V) takes place, for example, in the presence of a base and preferably in aqueous solution with an alkali metal hydroxide.

Compounds of general formula (V) are then reacted in the manner of a Robinson annellation with a CH acidic carbonyl compound and preferably with an acetoacetic acid ester derivative of general formula (VI) according to the following reaction scheme:

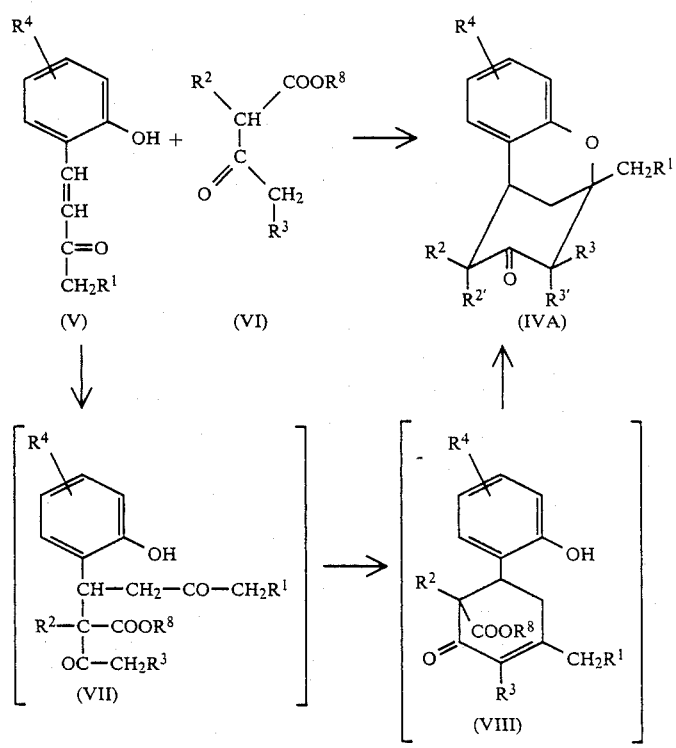

wherein $R^1$ is a hydrogen atom or a $C_1$-$C_4$-alkyl radical, $R^2$ and $R^{2'}$ are hydrogen atoms or $C_1$-$C_4$-alkyl radicals, whereby in (IVA) at least one of them is a hydrogen atom, $R^3$ and $R^{3'}$ are hydrogen atoms or $C_1$-$C_4$-alkyl or phenyl radicals, whereby in (IVA) at least one of them is a hydrogen atom, $R^4$ is a hydrogen, chlorine or bromine atom, a $C_1$-$C_2$-alkoxy or $C_1$-$C_4$-alkyl radical or a hydroxyl group, whereby the substituent can be in the ortho- or para-position to the oxygen atom, and $R^8$ is a $C_1$-$C_4$-alkyl or tert.-butyl radical.

The reaction of compounds of general formulae (V) and (VI) is preferably carried out in a $C_1$-$C_4$ alcohol in the presence of a base. The reaction is favourably carried out in anhydrous ethanol in the presence of sodium ethylate or in ethanol after the addition of a small amount of a highly concentrated aqueous solution of an alkali metal hydroxide. The reaction can be carried out at a temperature of from 0° to 100° C. but preferably either at ambient temperature or at the boiling point of the solvent.

The reaction proceeds via a Michael addition to give an intermediate probably of the general formula (VII) which is then cyclised to a cyclohexane derivative probably of general formula (VIII), subsequently decarboxylated and, with the phenolate, there is formed a ring of the compound type of general formula (IVA).

there is used a cyclic ketone, for example of the general formula (IXA) or (IXB), as has already been demonstrated for simple representatives (see F. Eiden and P. Gmeiner, Arch. Pharm. 319, 431/1986):

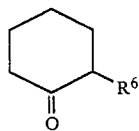 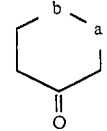

(IXA)   (IXB)

wherein $R^6$ is a hydrogen atom or a $C_1$-$C_4$-alkyl radical, a is an oxygen or sulphur atom and b is $CH_2$ or a is $CH_2$ and b is an oxygen or sulphur atom.

In the following reaction scheme, $R^3$ and $R^{3'}$ are hydrogen atoms or $C_1$-$C_4$-alkyl or phenyl radicals, whereby in (IVB) or (IVC) at least one of them is a hydrogen atom, $R^4$ is a hydrogen, chlorine or bromine atom, a $C_1$-$C_2$-alkoxy or $C_1$-$C_4$-alkyl radical or a hydroxyl group, whereby the substituents can be in the ortho- or para-position to the oxygen atom, and $R^6$ and $R^{6'}$ are hydrogen atoms or $C_1$-$C_4$-alkyl radicals, whereby in (IVC) at least one of them is a hydrogen atom:

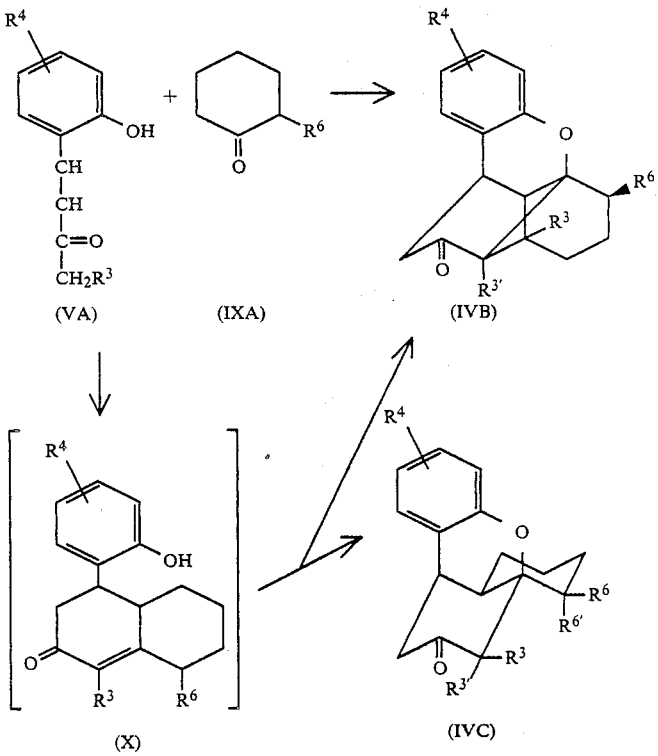

As the substituent pattern shows, in (VII) the carbonyl group of the original enone (V) reacts with the $CH_2R^3$ radical of the acetoacetic acid part. Since ketones of general formula (IV) with an additional ring via the radicals $R^1$ and $R^5$ or $R^{5'}$ arise in a somewhat different way, there is used the formula of a subgroup of (IV), which is designated (IVA).

Instead of the acetoacetic acid ester of general formula (VI), there can also be used other CH-acidic carbonyl compounds. An additional ring is obtained in the condensation product of general formula (IV) when The reaction of compounds of general formula (VA) with those of general formula (IX) generally require stronger bases than the reaction with compounds of general formula (VI). Therefore, the reaction is preferably carried out in an aprotic solvent with a strong base. Thus, for example, it can be readily carried out in dimethyl sulphoxide with sodium hydride as base. In this case, the Michael addition takes place on the less substituted $\alpha$-carbon atom of the cyclic ketone and the ring formation to the probable intermediate (X) takes place between the carbonyl group of the original ketone (IX) and the CH₂ group originating from the enome (VA). This intermediate further reacts immediately with ring closure to give (IVB) and/or (IVC). These two compounds differ in the connection of rings B and C which is trans in the case of (IVB) and is in the case of (IVC). In the case of this reaction, α-methylcyclohexanone exclusively gives the trans product (IVB). In almost all cases, the trans product preponderates strongly in the case of alkaline condensation. However, the cis-linked products can be obtained according to a special process by epimerisation from the trans products (IVB) with acids or Lewis acids. It is preferable to use concentrated hydrochloric acid in tetrahydrofuran, there thus being obtained about 95% of cis (IVC) and 5% trans (IVB).

A further variation of the structure can be achieved by using a derivative of (VA) protected on the hydroxyl group. In this case, the primary condensation in the Michael addition takes place on the more strongly hindered 2-position of the α-alkylcyclohexane. After removal of the protective group from the hydroxyl group in acid solution, ring formation takes place, a separable mixture of B/C-trans and B/C-cis products thereby being obtained which bears the alkyl radical in the 9a-position (compounds of general formula IVD and IVE):

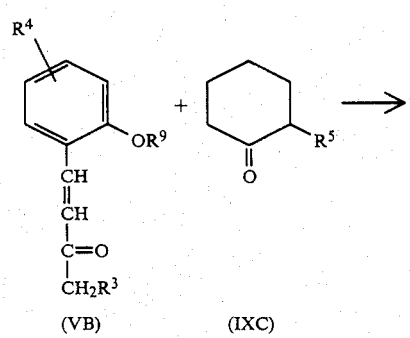

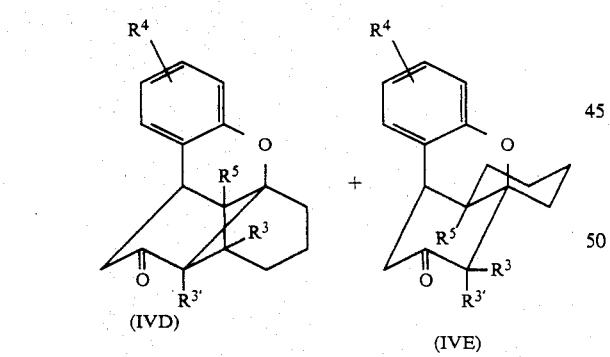

wherein $R^3$ and $R^{3'}$ are hydrogen atoms or $C_1$–$C_4$-alkyl or phenyl radicals, whereby in (IVD) and (IVE) at least one of them is a hydrogen atom, $R^4$ is a hydrogen, chlorine or bromine atom or a $C_1$–$C_2$-alkoxy or $C_1$–$C_4$-alkyl radical, whereby the substituent can be in the ortho- or para-position to the oxygen atom, $R^5$ is a $C_1$–$C_4$-alkyl radical and $R^9$ is a temporary protective group for the hydroxyl group, for example a silyl, acetyl, methoxymethyl or methoxyethoxymethyl radical.

As protective group, there is preferably used the methoxyethoxymethyl (MEM) radical which can be introduced by reacting substituted salicylaldehydes or compounds of general formula (VA) with methoxyethoxymethyl chloride in the presence of an organic base. In this case, splitting off takes place with an acid.

When $R^5$ is a hydrogen atom (in the case of reaction with cyclohexanone), only one diastereomer is obtained, namely (IVE).

Instead of cyclic ketones, there can also be used the pyrrolidine enamines of the ketones, such as the compound of the formula:

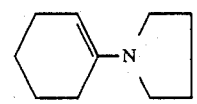

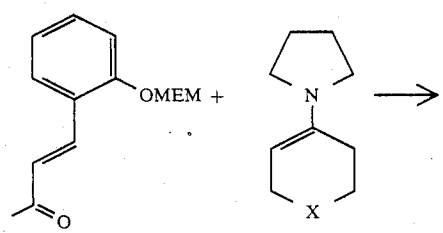

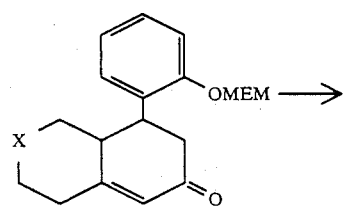

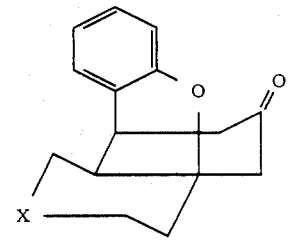

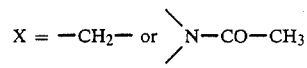

In the case of the use of heterocyclic ketones of the structural type (IXB), the reaction takes place analogously to that in the case of ketones of general formula (IXA). In the case of the use of asymmetric ketones of general formula (IXB), for example 5,6-dihydro-2H-thiopyran-3-(4H)-one, besides the various ring connections of the rings B/C, there can also be formed regioisomers with regard to the position of the sulphur atom. Thus, in the case of the reaction of compounds of general formula (V) with 5,6-dihydro-2H-thiopyran-3(4H)-one, there can be obtained isomeric products, for example compounds (IVF, G, H and I), in pure form.

(IVF)

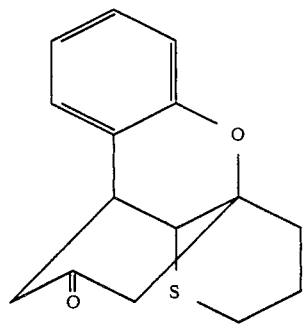

(IVG)

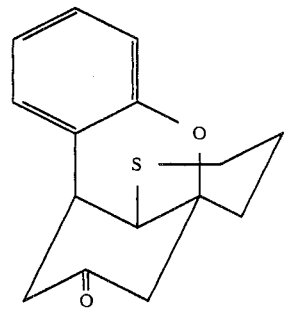

(IVH)

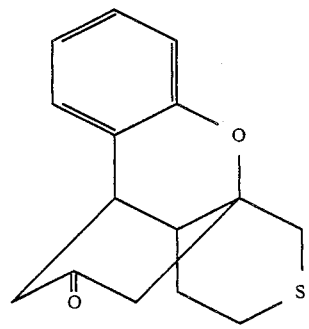

(IVI)

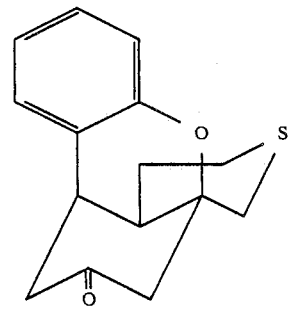

Nitrogen can be introduced into ring C, for example by use of a 4-piperidone derivative, for example with 1,2,5,6-tetrahydro-1-acetyl-4-pyrrolidinopyridine as enamine of a cyclic ketone.

As already mentioned, the compounds according to the present invention of general formula (I), as well as the compounds of general formula (IV), are highly effective analgesics with low side effects. When taking these compounds, unlike the taking of known opiates, they do not give rise to addiction.

For the pharmacological investigations described in the following, there were used male NMRI mice with a weight of from 15 to 30 g. The animals were kept under usual laboratory conditions, randomised and subjected to a light-dark change with a 12 hour rhythm. They were given a standard feed and water ad libitum up to the commencement of the experiments.

The test compounds were administered in a volume of 10 ml./kg./body weight per mouse. As carrier, there was used physiological sodium chloride solution or a suspension of 0.5% tragacanth in physiological sodium chloride solution.

The experimental results are given as average values with a mean error of the average value ($\bar{x} \pm$ S.E.M.). The ED$_{50}$ values were calculated according to Litchfield and Wilcoxon (J. Pharmacol. Exp. Ther., 96, 99/1949). The compounds were thereby tested in 4 dosages (p$\leq$0.5).

For the significance calculation, there was used Student's t test (see Angewandte Statistik, pub. Stringer Verlag, Berlin, Heidelberg, 242/1983), as well as the range sum test of Mann and Withney (Ann. Math. stat., 50, 1818/1947).

1. Analgesic effectiveness.

1.1. In the acetic acid writhing test (see R. Koster et al., Fed. proc., 18, 412/1954), the typical stretching movements referred to as "writhing", were produced by the intraperitoneal administration of a 0.6% acetic acid solution. 30 minutes previously, the substance to be tested was administered subcutaneously (s.c.) or orally (p.c.) to the animals. 3 minutes after administration of the acetic acid solution, the total number of stretching movements in a period of time of 10 minutes was ascertained. From the decrease of the stretching reactions due to the action of the test compound in comparison with non-pretreated control groups, there was determined the percentage inhibition action. The graphically determined ED$_{50}$ values (decrease of the extension reactions to 50% of the control group; 6 to 12 animals per dosage group) are given in the following Table I.

TABLE I

| compound of Example No. | s.c. | p.o. | quotient p.o./s.c. |
|---|---|---|---|
| 6 | 13.0 (6.7–25.1) | 21.5 (9.2–50.3) | 1.65 |
| ±9 | 13.8 (8.0–23.7) | 20.0 (10.2–39.4) | 1.45 |
| tramadol | 7.8 (5.2–11.8) | 10.2 (5.1–19.6) | 1.31 |

In this test, the compound of Example 12 showed, at a dosage of 50 mg./kg. s.c., an inhibiting action of 79% and, at a dosage of 25 mg./kg. s.c., an inhibiting action of 24%.

It can be seen that the action of the compounds according to the present invention is comparable with that of the known compound tramadol, i.e. 2-[(dimethylamino)-methyl]-1-(3-methoxyphenyl)-cyclohexanol. Like tramadol, orally they are somewhat less effective than subcutaneously.

1.2. Naloxone-antagonistic action in the writhing test.

20 Minutes before the subcutaneous administration of the test compounds, the animals were given 20 mg./kg. naloxone hydrochloride subcutaneously. The further carrying out of the experiments was as described above. The results obtained are given in the following Table II.

TABLE II

| compound of Example No. | dosage mg/kg | % inhibition action ± SEM | | change in % |
|---|---|---|---|---|
| | | without naloxone | with naloxone | |
| 6 | 50 | 84.6 ± 7.7 | 91.8 ± 3.3 | 7.2 |

TABLE II-continued

| compound of Example No. | dosage mg/kg | % inhibition action ± SEM | | change in % |
|---|---|---|---|---|
| | | without naloxone | with naloxone | |
| | 25 | 58.9 ± 10.1 | 65.5 ± 6.5 | 6.6 |
| | 12.5 | 33.2 ± 3.2 | 39.7 ± 10.4 | 6.5 |
| ±9 | 50 | 84.9 ± 2.7 | 88.4 ± 11.6 | 3.5 |
| | 25 | 64.0 ± 5.0 | 80.1 ± 6.8 | 16.1 |
| | 12.5 | 57.0 ± 7.6 | 52.0 ± 1.5 | 5.0 |
| tramadol | 20 | 91.2 ± 2.0 | 60.5 ± 2.9 | 30.7 |
| | 10 | 69.4 ± 5.5 | 30.4 ± 9.9 | 39.0 |

It can be seen that the compounds according to the present invention do not lose their inhibitory action in the writhing test even in the case of pretreatment of the animals with naloxone. The difference of the percentage inhibitory action with and without naloxone treatment is statistically not significant (t=0.37–1.96, 0.1 < p < 0.7).

In contradistinction thereto, the inhibitory action of tramadol, which is regarded as being a weak naloxone antagonist, is, after pretreatment of the experimental animals with naloxone, statistically significantly lower (t=8.41, p≦0.01).

1.3. Hot plate test.

This test is described by P. A. J. Janssen and A. Jageneau (J. Pharm. Pharmacol., 9, 381/1957).

30 and 60 minutes after the subcutaneous administration of the test compounds, the experimental animals were placed on a metal plate, the surface temperature of which was kept constant at 54° C. The time was measured up to the commencement of a pain reaction (standing on the rear paws with licking and rubbing togeth4er of the front paws or jumping). In a preceding test, the average reaction time of the animals was determined from three measurements at intervals of, in each case, 15 minutes.

The ED$_{50}$ values given hereinafter are defined as being the 50% increase of the reaction time due to the action of the test compound in comparison with the average value from the preceding test on the untreated animals (5 to 50 animals/dosage group). The following results were obtained:

compound of Example 9: 12.0 mg./kg. (4.2–34.4)
compound of Example 6: 13.8 mg./kg. (5.7–33.1).

In the hot plate test, the tested compounds according to the present invention show results comparable with those in the writhing test (subcutaneous administration).

2. Development of dependency.

Withdrawal jumps of the mouse (see J. K. Saelens et al., Arch. Int. Pharmacodyn. Ther., 190, 213/1971).

Mice which were dependent upon morphine or other opiates react, when treated with morphine antagonists, with a flight reaction (see F. Huidobro and C. Maggiolo, Arch. Int. Pharmacodyn. Ther., 158, 97/1965); E. L. Way et al., Science, 162, 1290/1968). This flight reaction manifests itself in very vigorous jumping reactions which continue for about 10 minutes. From the number of reacting animals and especially from the jump frequency per animal, there can be deduced the strength of the withdrawal symptoms and thus the degree of dependency upon the test compound. Carrying out of the test:

The test and standard compounds were administered subcutaneously according to the scheme shown in the following Table III in increasing dosages over the course of 2 days.

TABLE III

| dosage mg/kg h | 10.00 | 11.00 | 12.00 | 14.00 | 16.00 |
|---|---|---|---|---|---|
| 1st day | 6.25 | 12.5 | 25.0 | 50.0 | 50.0 |
| 2nd day | 50.0 | — | 50.0 | naloxone 39 mg/kg | — |

For the provocation of the withdrawal jumps, the animals received intraperitoneally, 2 hours after the last compound administration, 30 mg./kg. naloxone hydrochloride.

Immediately after the administration of the naloxone, the animals were placed individually in a 5 liter glass beaker. Subsequently, the number of jump movements was recorded during the course of 10 minutes. For evaluation, the number of animals reacting the withdrawal jumps, as well as the average number of jumps per animal, was used.

The animals of the naloxone control group were, up to the administration of naloxone, treated with a 0.9% aqueous solution of sodium chloride (6 animals/dosage group).

The results obtained are summarised in the following Table IV.

TABLE IV

| test compound | number of animals | % of reacting animals | average number of jumps/animal/ 10 minutes |
|---|---|---|---|
| NaCl control | 6 | 0 | 0 |
| Example 6 | 6 | 0 | 0 |
| ± Example 9 | 6 | 0 | 0 |
| tramadol HCl | 6 | 83.3 | 12.5 |
| morphine HCl | 6 | 100 | 38.8 |

It can be seen that the compounds according to the present invention do not possess any dependency potential.

3. Influencing of the amphetamine group toxicity.

There was investigated the influence of the test compounds on the mortality of amphetamine-treated, aggregated mice. The dosaging of d-amphetamine was 15 mg./kg., which should permit the recognition not only of a synergism but also of an antagonism towards a sympathomimetic compound. Carrying out the experiment:

30 minutes after the subcutaneous administration of the test substance, the animals received subcutaneously 15 mg./kg. of d-amphetamine sulphate. The number of dead animals was recorded after 2, 4 and 7 hours. For the maintenance of the group size, the dead animals were replaced by untreated animals (6 animals/dosage group). The results obtained are summarised in the following Table V.

TABLE V

| test compound | dosage mg/kg | number of animals | % of deceased animals | | | % total |
|---|---|---|---|---|---|---|
| | | | after 2 hrs. | after 4 hrs. | after 7 hrs. | |
| amphetamine control group | 15 mg. s.c. | 12 | 0 | 33 | 0 | 33.3 |
| Example 6 | 50 mg. | 6 | 0 | 16.7 | 0 | 16.7 |
| | 25 mg. | 6 | 0 | 0 | 16.7 | 16.7 |
| ± Example 9 | 50 mg. | 6 | 0 | 0 | 33.3 | 33.3 |
| | 25 mg. | 6 | 16.7 | 0 | 0 | 16.7 |

It can be seen that the compounds according to the present invention display neither a synergistic nor an antagonistic action towards amphetamine.

4. Influencing of hexobarbital narcosis.

The test compounds were administered subcutaneously to 5 animals per dosage group. After 30 minutes, 100 mg./kg. hexobarbital sodium was administered intraperitoneally. 2 to 3 minutes after this injection, the animals allowed themselves to be laid on their backs. For each animal, there was measured the time in minutes from the commencement of the back position up to the time when the animals themselves twice successively again assumed the abdominal position. The results obtained are summarised in the following Table VI.

TABLE VI

| test compound | dosage mg/kg | period of narcosis in min. ± SEM | change with regard to hexabarbital sodium in min. | P |
|---|---|---|---|---|
| ± Example 9 | 50 sc | 39 ± 12.4 | −53.4 | p 0.025 |
|  | 25 sc | 63 ± 21.0 | −29.4 | n.s. |
| codeine phosphate | 50 sc | 143.6 ± 10.5 | +51.2 | p 0.025 |
| amphetamine sulphate | 1.0 sc | 49.2 ± 14.6 | −43.2 | p 0.05 |
| hexobarbital | 100 ip | 92.4 ± 17.1 | — | | n.s. = not significant.

It can be seen that, as was to have been expected, the compound of Example 9 brings about, at a dosage of 50 mg./kg., a statistically verified shortening of the period of narcosis.

5. Testing for ataxia.

There was used the rotating rod test (see F. Gross et al., Schweiz. Med. Wschr., 85, 305/1955).

5 animals per dosage group were trained to keep themselves on a horizontally rotating rod made of synthetic resin (16 rpm). 40, 80 and 120 minutes after the subcutaneous administration of the test compounds, the animals were again tested. From the number of animals which fell off prematurely, there was determined the disturbance of the movement coordination. The results obtained are summarised in the following Table VII.

TABLE VII

| test compound | dosage mg/kg | change of the maintenance time in % compared with the control group | | |
|---|---|---|---|---|
| | | after 40 min. | after 80 min. | after 120 min. |
| Example 6 | 50 | −17 | 0 | −8 |
|  | 25 | 0 | −8 | 0 |
| Example 9 | 50 | 0 | 0 | −2 |
|  | 25 | −13 | −17 | −12 |
| diazepam | 5 | −87 | −73 | −22 |
| phenobarbital | 30 | −29 | −21 | −37 |
|  | 50 | −54 | −46 | −42 |

It can be seen that the compounds according to the present invention have no noteworthy influence on the movement coordination of the animals.

6. Tonus reduction on striated musculature.

The test used is described by J. P. Chambon et al. (Arzneimittelforschung (Drug Research), 35 (II), (10), 1572/1985).

5 animals per dosage group were placed with their front paws on a horizontal metal rod (diameter 3 mm., length 20 cm.) which was fixed 30 cm. above a laboratory bench. Mice with normal muscle tonus climbed within 5 seconds on to the rod with at least one rear paw.

40, 80 and 120 minutes after the subcutaneous administration of the test compound, the animals were again tested for this ability and the number of incapable animals was recorded.

The results of this investigation are comparable with the values which were obtained in the testing for ataxia. Thus, the compounds of Examples 6 and 9 showed, at a dosage of 50 mg./kg., a muscle-relaxing action of only 20% and at 25 mg./kg. of 13%.

At a dosage of 5 mg./kg., diazepam showed a relaxing action of 93%.

7. Antidepressive action.

There was used the reserpine reversal test (see G. Zettler, K. Mahler and F. Daniel, Naunyn-Schmiedeberg's Arch. Exp. Path. Pharmacol., 238, 468/1960; ibid. 236, 422/1958). 30 minutes after the subcutaneous administration of the test compounds, the animals (6 animals per dosage group) received subcutaneously 40 mg./kg. tetrabenazine dissolved in 0.5% aqueous ascorbic acid solution. 30 and 60 minutes after the tetrabenazine administration, the animals were placed on a vertical rod (length 90 cm., diameter 1.5 cm., coiled round with 0.2 cm. thick thread) and observed for 30 seconds. Those animals which remained motionless during this time were evaluated as being cataleptic. Previously, the degree of ptosis was assessed.

The compounds of Examples 6 and 9 at a dosage of 50 and 25 mg./kg. did not influence the symptoms induced by tetrabenazine (catalepsy, ptosis).

Renewed opiate receptor affinity measurements have shown that the active materials have only a weak affinity and consequenty also do not have a C-affinity. It is possible that a completely different activity mechanism is present.

The compounds according to the present invention can be administered orally or parenterally, for example intravenously, subcutaneously, intramuscularly or intracutaneously. The dosage depends, in the first place, upon the specific form of administration and upon the purpose of the therapy. The size of the individual dosages, as well as the scheme of administration, can best be determined on the basis of an individual assessment of the particular illness. Normally, the individual dosage is in the range of from about 10 to 80 mg. and preferably in the range of from about 20 to 60 mg.

The acute toxicity of the compounds according to the present invention is low ($LD_{50} > 250$ mg./kg. in the case of rats).

For therapeutic use, the compounds of the present invention are generally formulated as pharmaceutical compositions which contain at least one of the compounds of general formula (I) and/or compounds of general formula (IV), optionally together with conventional carriers and/or additives.

Compositions for parenteral administration usually consist of an aqueous solution or an oily suspension of the active material. The active material is thereby dissolved in water or in a carrier, such as a polyhydroxy aliphatic alcohol, for example glycerol, propylene glycol or polyethylene glycol, or a mixture thereof.

Compositions for oral administration can be, for example, in the form of tablets, pastilles, capsules, powders, syrups, elixirs or solutions, preferred oral compostions being tablets and capsules. Compositions for oral administration can contain conventional excipients, such as binding agents (for example syrup, acacia, gelatine, sorbitol, tragacanth or polyvinylpyrrolidone). There can also be present filling agents, for example lactose, sugar, maize starch, calcium phosphate, sorbitol or glycine, lubricating agents, such as magnesium stearate, talc, polyethylene glycol or silicon dioxide, disintegration agents, for example starch, and surface-active agents, for example sodium lauryl sulphate.

The following Examples are given for the purpose of illustrating the present invention. The NMR data given in the Examples are δ-values.

EXAMPLES

A. Process for the preparation of intermediates of general formula (I) with X=NH and Y=CO or X=CO and Y=NH General Procedure (Schmidt reaction (AV-1))

0.045 mole of a ketone of general formula (IV) and 0.062 mole sodium azide were dissolved in 33 ml. glacial acetic acid and mixed dropwise with 6.6 ml. concentrated sulpuric acid. After cessation of foaming up, a further 10 ml. of glacial acetic acid were added thereto and the reaction mixture was stirred for 20 minutes at ambient temperature and for 2 to 3 hours at 45° to 50° C. The reaction mixture was subsequently carefully added to 350 ml. of a 10% aqueous solution of sodium carbonate, the solution was exhaustively shaken out with diethyl ether and the organic phases were washed with a little 2N aqueous sodium hydroxide solution. After drying the organic phase, it was evaporated on a rotary evaporator (fraction A). The combined aqueous solutions were neutralised, again exhaustively shaken out with diethyl ether and the ethereal solution dried and evaporated (fraction B).

EXAMPLE 1

According to general process AV-1, from 2H-5,6-dihydro-2-methyl-2,6-methanol-1-benzoxazin-4(3H)-one (for the preparation thereof see T. A. Forster and I. M. Heilbron, J. Chem. Soc. London, 125 and 340/1924; as well as R. Kuhn and O. Weiser, Chem. Br., 88, 1601/1955), there were obtained 5.08 g. of fraction A which contains compounds 10 and 11, according to $^1$H-NMR, in a ratio of 6:5 (yield of compounds 10+11=52% of theory). By repeated recrystallisation from ethyl acetate, there was obtained pure compound 11. 5H-2,3,6,7-Tetrahydro-2-methyl-2,7-methano-1,4-benzoxazonin-5-one (compound 11) was obtained in the form of colourless crystals; m.p. 165° C. (for compound 10 see Example 2).

Analysis for $C_{13}H_{15}NO_2$ (M.W. 217.3): calc.: C 71.8%; H 6.96%; N 6.45%. found: 71.7%; 6.91%; 6.46%.

Molecular weight 217 (ms).

IR (KBr): 3200, 3080, 2980, 1650, 1580 cm$^{-1}$.

$^1$H-NMR (CDCl$_3$): 1.4 (s, 3H), 2.1 (d, J=3 Hz, 2H), 2.85 (d, J=5 Hz, 2H), 3.1-3.4 (m, 3H), 6.05 (m, 1H, H/D exchange), 6.7-7.3 (m, 4H) ppm.

EXAMPLE 2

The mother liquor of the ethyl acetate recrystallisation obtained in Example 1 was evaporated and the residue recrystallised from toluene. There were obtained colourless crystals of 4H-2,3,6,7-tetrahydro-2-methyl-2,7-methano-1,5-benzoxazonin-4-one (compound 10); m.p. 146° C.

Analysis for $C_{13}H_{15}NO_2$ (M.W. 217.3): calc.: C 71.8%; H 6.96%; N 6.45%. found: 71.6%; 6.92%; 6.47%.

Molecular weight 217 (ms).

IR (KBr): 3200, 3080, 2980, 1650, 1580 cm$^{-1}$.

$^1$H-NMR (CDCl$_3$): 1.5 (s, 3H), 2.1 (d, J=3 Hz, 2H), 2.8 (s, 2H), 3.2 (m, 2H), 3.5 (m, 1H), 6.0 (m, 1H, H/D exchange), 6.7-7.35 (m, 4H).

From fraction B of Example 1, by recrystallisation from ethanol, there was obtained a yield of 21% of theory of colourless crystals of 2H-3,4,5,6-tetrahydro-6-(2-hydroxphenyl)-4-methyl-azepin-2-(1H)-one; m.p. 187° C.

EXAMPLE 3

According to general procedure AV-1, from 2H-5,6-dihydro-2,5-dimethyl-2,6-methano-1-benzoxazin-4-(3H)-one there was obtained a fraction A which, after recrystallisation from ethyl acetate, gave colourless crystals of 4H-2,3,6,7-tetrahydro-2,6-dimethyl-2,7-methano-1,5-benzoxazonin-4-one in a yield of 6.34 g. (61% of theory); m.p. 164° C.

Analysis for $C_{14}H_{17}NO_2$ (M.W. 231.3): calc.: C 72.7%; H 7.41%; N 6.06%. found: 73.0%; 7.14%; 6.01%.

Molecular weight 231 (ms).

IR (KBr): 3280, 3040, 2950, 1650, 1580 cm$^{-1}$.

$^1$H-NMR (CDCl$_3$): 1.3 (d, J=7 Hz, 3H), 1.45 (s, 3H), 2.15 (d, J=7 Hz, 2H), 2.85 (s, 2H), 2.9 (m, 1H), 3.85 (m, 1H), 5.2 (m, H/D exchange), 6.7-7.35 (m, 4H) ppm.

EXAMPLE 4

According to general procedure AV-1, from 2H-5,6-dihydro-8-methoxy-2,5-dimethyl-2,6-methano-1-benzoxazin-4(3H)-one, there were obtained, after recrystallisation from ethyl acetate, colourless crystals of 4H-2,3,6,7-tetrahydro-9-methoxy-2,6-dimethyl-2,7-methano-1,5-benzoxazonin-4-one in a yield of 8.25 g (70.2% of theory); m.p. 194° C.

Analysis for $C_{15}H_{19}NO_3$ (M.W. 261.3): calc.: C 68.9%; H 7.33%; N 5.36%. found: 69.1%; 7.15%; 5.43%.

Molecular weight 261 (ms).

IR (KBr): 3210, 3080, 2990, 1655 cm$^{-1}$.

$^1$H-NMR (CDCl$_3$): 1.3 (d, J=7 Hz, 3H), 1.4 (s, 3H), 2.15 (d, J=4 Hz, 2H), 2.8 (s, 2H), 2.85 (m, 1H), 3.75 (s, 3H), 3.8 (m, 1H), 5.45 (m, 1H, H/D exchange), 6.55 (m, 1H), 6.8 (d, J=2 Hz, 2H).

EXAMPLE 5

As a modification of general procedures AV-1, B/C-trans-1,2,3,4,4a,9a-hexahydro-4-methyl-4a,9-propanoxanthen-12-one (preparation see E Eiden and P. Gmeiner, Arch. Pharm., 319, 431/1986) was not reacted at 45° to 50° C. but at ambient temperature for 90 minutes and worked up in the described manner. From fraction A there was obtained 6.34 g. (52% of theory) of colourless crystals of a mixture of B/C-trans-1,2,3,4,4a,-9a-hexahydro-4-methyl-4a,9-(2-azabutano)-xanthen-13-one and B/C-trans-1,2,3,4,4a,9a-hexahydro-4-methyl-4a,9-(3-azabutano)-xanthen-12-one. This mixture was further worked up, without further separation, to give a compound of type (I).

B. Process for the Preparation of Pharmacologically Effective Products of General Formula (I), $R^7 = H$ General Procedure (reduction) (AV-2)

0.005 mole of a lactam of general formula (I), wherein X is NH and Y is CO or X is CO and Y is NH, in 25 ml. dry tetrahydrofuran was added dropwise, with cooling and stirring, to a suspension of 1.75 g. (0.047 mole) lithium aluminium hydride in 20 ml. anhydrous tetrahydrofuran. After stirring for 1 hour at ambient temperature and heating under reflux for 3 hours, 10 ml. water were carefully added dropwise thereto, the precipitate obtained was separated off and the filtrate was evaporated in a rotary evaporator. The residue was distilled in a bulbed tube distillation apparatus.

EXAMPLE 6

According to general procedure AV-2, from 4H-2,3,6,7-tetrahydro-2-methyl-2,7-methano-1,5-benzoxazonin-4-one (10) there was obtained 0.73 g. (74% of theory) of a colourless liquid of 2,3,4,5,6,7-hexahydro-2-methyl-2,7-methano-1,5-benzoxazonine (1); b.p. 120° C./0.001 mm.Hg (bulbed tube).

Analysis for $C_{13}H_{17}NO$ (M.W. 203.3): calc.: C 76.8%; H 8.43%; N 6.89%. found: 76.5%; 8.59%; 7.09%.

Molecular weight 203 (ms).

IR (NaCl): 3020, 2960, 1590 cm$^{-1}$.

$^1$H-NMR (CDCl$_3$): 1.5 (s, 3H), 1.73 (s-broad, 1H, H/D-exchange), 1.9 (t, J=5 Hz, 2H), 2.15 (m, 2H), 2.6–3.4 (m, 5H), 6.75–7.35 (m, 4H) ppm.

EXAMPLE 7

According to general procedure AV-2, from 5H-2,3,6,7-tetrahydro-2-methyl-2,7-methano-1,4-benzoxazonin-5-one (11), there was obtained 0.79 g. (77.5% of theory) of a colourless liquid of 2,3,4,5,6,7-hexahydro-2-methyl-2,7-methano-1,4-benzoxazonine (2); b.p. 120° C./0.001 mm.Hg (bulbed tube).

Analysis for $C_{13}H_{17}NO$ (M.W. 203.3): calc.: C 76.8%; H 8.43%; N 6.89%. found: 76.7%; 8.51%; 6.87%.

Molecular weight 203 (ms).

IR (NaCl): 3020, 2960, 1590 cm$^{-1}$.

$^1$H-NMR (CDCl$_3$): 1.4 (s, 3H), 1.67 (s-broad, 1H, H/D-exchange), 1.8–2.2 (m, 4H), 2.65–3.3 (m, 3H), 2.95 (s, 2H), 6.7–7.3 (m, 4H) ppm.

EXAMPLE 8

1.08 g. of the isomeric mixture of compounds 10 and 11 from Example 1 was reduced according to general procedure AV-2 and the reaction products separated by column chromatography (silica gel 60, elution agent chloroform/methanol 8:2 v/v). There were obtained 320 mg. of compound 2 and 190 mg. of compound 1 in pure form.

EXAMPLE 9

According to general procedure AV-2, from 4H-2,3,6,7-tetrahydro-2,6-dimethyl-2,7-methano-1,5-benzoxazonin-4-one (see Example 3) there was obtained 0.069 g. (63.5% of theory) of a colourless liquid of 2,3,4,5,6,7-hexahydro-2,6-dimethyl-2,7-methano-1,5-benzoxazonine (5); b.p. 145° C./0.005 mm.Hg (bulbed tube).

Analysis for $C_{14}H_{19}NO$ (M.W. 217.3): calc.: C 77.4%; H 8.81%; N 6.45%. found: 77.7%; 9.02%; 6.31%.

Molecular weight 217 (ms).

IR (NaCl): 3020, 2960, 1590 cm$^{-1}$.

$^1$H-NMR (CDCl$_3$): 1.25 (d, J=7 Hz, 3H), 1.45 (s, 3H), 1.5 (s-broad, 1H, H/D exchange), 1.85–2.25 (m, 4H), 2.7–3.3 (m, 4H), 6.7–7.35 (m, 4H), ppm.

EXAMPLE 10

According to general procedure AV-2 but with the addition of 0.67 g. (0.005 mole) aluminum chloride and heating for 12 hours, from 4H-2,3,6,7-tetrahydro-9-methoxy-2,6-dimethyl-2,7-methano-1,5-benzoxazonin-4-one (from Example 4) there was obtained 0.67 g. (54.3% of theory) of colourless crystals of 2,3,4,5,6,7-hexahydro-9-methoxy-2,6-dimethyl-2,7-methanol-1,5-benzoxazonine (7); m.p. 61° C.; b.p. 160° C./0.01 mm.Hg (bulbed tube).

Analysis for $C_{15}H_{21}NO_2$ (M.W. 247.3): calc.: C 72.84%; H 8.56%; N 5.66%. found: 72.97%; 8.51%; 5.75%.

Molecular weight 247 (ms).

IR (NaCl): 3000, 1605 cm$^{-1}$.

$^1$H-NMR (CDCl$_3$): 1.2 (d, J=7 Hz, 3H), 1.35 (s-broad, 1H, H/D exchange), 1.4 (s, 3H), 1.8–2.2 (m, 4H), 2.65–3.2 (m, 4H), 3.8 (s, 3H), 6.65 (d, J=2 Hz, 1H), 6.8 (s, 2H) ppm.

EXAMPLE 11

According to general procedure AV-2, 1.3 g. (0.005 mole) of the isomeric mixture from Example 5 was reduced. The mixture obtained was separated on a Chromatron (Harrison Research Model 7924 T) on silica gel 60 PF 254 (layer thickness 2 mm., elution agent methylene chloride/methanol 95:5 v/v) and the first fraction subsequently distilled in a bulbed tube. There was obtained 0.5 g. (39% of theory) of a colourless liquid of B/C-trans-1,2,3,4,4a,9a-hexahydro-4-methyl-4a,9-(2-azabutano)-xanthene (9); b.p. 220° C./0.005 mm.Hg (bulbed tube).

Analysis for $C_{17}H_{23}NO$ (M.W. 257.4): calc.: C 79.3%; H 9.01%; N 5.44%. found: 79.3%; 9.01%; 5.74%.

Molecular weight 257 (ms).

IR (NaCl): 2960, 590 cm$^{-1}$.

$^1$H-NMR (CDCl$_3$): 1.05 (d, J=6 Hz, 3H), 1.1–2.2 (m, 10H), 1.5 (s, 1H, H/D-exchange), 2.8 (t, J=7 Hz, 2H), 2.9 (m, 1H), 3.12 (s, 2H), 6.65–7.25 (m, 4H) ppm.

EXAMPLE 12

The second fraction of the Chromatron separation of Example 11 gave, after distillation, 0.18 g. (14% of theory) of B/C-trans-1,2,3,4,4a,9a-hexahydro-4-methyl-4a,9-(3-azabutano)-xanthene (8); b.p. 205° C./0.005 mm.Hg.

Analysis for $C_{17}H_{23}NO$ (M.W. 257.4): calc.: C 79.3%; H 9.01%; N 5.44%. found: 79.0%; 9.38%; 5.02%.

Molecular weight 257 (ms).

IR (NaCl): 2960, 1590 cm$^{-1}$.

$^1$H-NMR (CDCl$_3$): 1.05 (d, J=6 Hz, 3H), 1.25–2.3 (m, 11H), 2.7 (t, J=6 Hz, 2H), 2.8 (m, 1H), 3.25 (d, J=3 Hz, 2H), 6.7–7.25 (m 4H), ppm.

C. Process for the Preparation of Methylamine of General Formula (I), $R^7 = CH_3$

General Procedure (AV-3)

6.5 ml. of a 37% aqueous solution of formaldehyde were added dropwise to a solution of 0.005 mole of amine of general formula (I) ($R^7 = H$) in 3 ml. formic acid and the reaction mixture subsequently stirred for 90 minutes at 95° C. The reaction mixture was then rendered alkaline with sodium hydroxide, shaken out with diethyl ether and the ethereal phase evaporated. The residue was distilled in a bulbed tube distillation apparatus.

EXAMPLE 13

According to general procedure AV-3, from 2,3,4,5,6,7-hexahydro-2-methyl-2,7-methano-1,5-benzoxazonine (1) there was obtained 0.93 g. (86% of theory) of a colourless liquid of 2,3,4,5,6,7-hexahydro-2,5-dimethyl-2,7-methano-1,5-benzoxazonine (3); b.p. 123° C./0.01 mm.Hg.

Analysis for $C_{14}H_{19}NO$ (M.W. 217.3): calc.: C 77.4%; H 8.81%; N 6.45%. found: 77.2%; 8.86%; 6.61%.

Molecular weight 217 (ms).

IR (NaCl): 2906, 1590 $cm^{-1}$.

$^1$H-NMR (CDCl$_3$): 1.45 (s, 3H), 1.75–2.2(m, 4H), 2.3 (s, 3H), 2.35–2.6 (m, 2H), 2.8–3.3 (m, 1H), 2.9 (m-centr., 2H), 6.7–7.3 (m, 4H) ppm.

EXAMPLE 14

According to general procedure AV-3, from 2,3,4,5,6,7-hexahydro-2-methyl-2,7-methano-1,4-benzoxazonine (2) there was obtained 1.0 g. (92% of theory) of a colourless liquid of 2,3,4,5,6,7-hexahydro-2,4-dimethyl-2,7-methano-1,4-benzoxazonine (4); b.p. 110° C./0.01 mm.Hg (bulbed tube).

Analysis for $C_{14}H_{19}NO$ (M.W. 217.3): calc.: C 77.4%; H 8.81%; N 6.45%. found: 77.2%; 8.79%; 6.64%.

Molecular weight 217 (ms).

IR (NaCl): 2960, 1590 $cm^{-1}$.

$^1$H-NMR (CDCl$_3$): 1.5 (s, 3H), 1.8–2.2 (m, 4H), 2.33 (s, 3H), 2.4–3.2 (m, 5H), 6.7–7.3 (m, 4H) ppm.

EXAMPLE 15

According to general procedure AV-3, from 2,3,4,5,6,7-hexahydro-2,6-dimethyl-2,7-methano-1,5-benzoxazonine (5) there was obtained 0.94 g. (82% of theory) of a colourless liquid of 2,3,4,5,6,7-hexahydro-2,5,6-trimethyl-2,7-methano-1,5-benzoxazonine (6); b.p. 120° C./0.01 mm.Hg (bulbed tube).

Analysis for $C_{15}H_{21}NO$ (M.W. 231.3): calc.: C 77.9%; H 9.15%; N 6.06%. found: 77.8%; 9.24%; 6.10%.

Molecular weight 231 (ms).

IR (NaCl): 2990, 2960, 1590 $cm^{-1}$.

$^1$H-NMR (CDCl$_3$): 1.28 (d, J=7 Hz, 3H), 1.4 (s, 3H), 1.8–2.2 (m, 4H), 2.33 (s, 3H), 2.4–3.1 (m, 4H), 6.7–7.35 (m, 4H) ppm.

EXAMPLE 16

General Procedure for the Preparation of Dibenzoyltartrates for Pharmacological Testing 0.00075 mole dibenzoyl-1-(+)-tartaric acid in 10 ml. dry diethyl ether was added dropwise to a solution of 0.0015 mole of amine in 10 ml. dry diethyl ether. The resultant precipitate was filtered off with suction and dried. The dibenzoyltartrates of compounds 1 and 5 were prepared in this way.

D. Process for the Preparation of Ketones of General Formula (IV) from Open-Chained Carbonyl Compounds

General Procedure AV-4

0.063 mole of sodium in 25 ml. ethanol was added dropwise to a solution of 0.03 mole of the enone of general formula (V) and 0.033 mole of the ketone of general formula (VI) in anhydrous ethanol, while cooling with ice water. The reaction mixture was further stirred at ambient temperature for 3 to 4 days and water added portionwise thereto until a slight turbidity was obtained.

EXAMPLE 17

According to general procedure AV-4,4-(2-hydroxyphenyl)-trans-3-buten-2-one was reacted with ethyl 2-methylacetoacetate. The resultant precipitate was separated off and recrystallised from methanol to give 2H-5,6-dihydro-2,5-dimethyl-2,6-methano-1-benzoxocin-4-(3H)-one in the form of colourless needles; m.p. 110° C.; yield 2.46 g. (38% of theory).

Analysis for $C_{14}H_{16}O_2$ (M.W. 216.3): calc.: C 77.7%; H 7.46%. found: 77.7%; 7.50%.

Molecular weight 216 (ms).

IR (KBr): 2980, 1710, 1595 $cm^{-1}$.

$^1$H-NMR (CDCl$_3$): 1.07 (d, J=7 Hz, 3H), 1.55 (s, 3H), 2.33 (d, J=3 Hz, 2H), 2.5–2.95 (m, 3H), 3.15 (q, J=3 Hz, 1H), 6.65–7.35 (m, 4H).

$^{13}$C-NMR (CDCl$_3$): 12.4 (q), 28.6 (q), 36.5 (t), 39.6 (d), 49.3 (d), 53.3 (t), 77.7 (s), 116.3 (d), 119.1 (d), 120.8 (s), 128.4 (d), 130.1 (d), 152.7 (s), 208.8 (s) ppm.

EXAMPLE 18

According to general procedure AV-4,4-(2-hydroxy-5-methoxyphenyl)-trans-3-butene-2-one was reacted with ethyl 2-methylacetoacetate. The precipitate formed was separated off and recrystallised from ethanol. There was obtained 2H-5,6-dihydro-8-methoxy-2,5-dimethyl-2,6-methano-1-benzoxocin-4-(3H)-one in the form of colourless needles; m.p. 98° C.; yield 3.30 g. (45% of theory).

Analysis for $C_{15}H_{18}O_3$ (M.W. 246.3): calc.: C 72.5%; H 8.12%. found: 72.6%; 7.90%.

Molecular weight 246 (ms).

IR (KBr): 2980, 1710, 1600 $cm^{-1}$.

$^1$H-NMR (CDCl$_3$): 1.1 (d, J=7 Hz, 3H), 1.5 (s, 3H), 2.25 (d, J=3 Hz, 2H), 2.55 (s-broad, 2H), 2.7 (m, 1H), 3.05 (q, J=3 Hz, 1H), 3.72 (s, 3H), 6.5 (q, J=2 Hz, 1H), 6.7 (s, 2H).

E. Process for the Preparation of Ketones of General Formula (IV) from Cyclic Ketones

General Procedure AV-5

0.03 mole of the cyclic ketone of general formula (IX) was stirred with 0.7 g. (0.03 mole) sodium hydride in 50 ml. dimethyl sulphoxide until the evolution of hydrogen had ceased (about 3 hours). Subsequently, 0.03 mole of the enone of general formula (V) and 0.7 g. (0.03 mole) sodium hydride in 50 ml. dimethyl sulphoxide were added thereto. After stirring for 14 hours at ambient temperature under an atmosphere of nitrogen, 500 ml. water were added thereto. The mixture was shaken out with diethyl ether and the extract washed with 2N aqueous sodium hydroxide solution and then with water. The organic phase was dried with anhydrous magnesium sulphate and evaporated.

EXAMPLE 19

According to general procedure AV-5, 3.3 g. 2-methylcyclohexanone were reacted with 7.5 g. 4-(2-methoxyethoxymethoxyphenyl)-trans-3-buten-2-one and the residue purified with a Chromatron (silica gel 60 PF 254, layer thickness 4 mm., elution agent petroleum ether/ethyl acetate (8:2 v/v). After distillation in a bulbed tube (b.p. 220° C./0.01 mm.Hg), there was obtained 2.3 g. (22.3% of theory) 4-(2-methoxymethoxymethoxyphenyl)-4a-methyl-2,3,4,4a,5,6,7,8-octahydronaphthalen-2-one. 1.38 g. (0.004 mole) of this compound was dissolved in 20 ml. tetrahydrofuran and 10 ml. concentrated hydrochloric acid added dropwise thereto. Subsequently, the reaction mixture was stirred for 4 days at ambient temperature and then evaporated in a vacuum. After crystallisation of the residue from methanol/water, there was obtained 0.82 g. (80.4% of theory) of colourless crystals of B/C-cis-1,2,3,4,4a,9a-hexahydro-9a-methyl-4a,9-propanoxanthen-12-one; m.p. 105° C.

Analysis for $C_{17}H_{20}O_2$ (M.W. 256.3): calc.: C 79.6%; H 7.86%. found: 79.8%; 7.73%.

Molecular weight 256 (ms).

IR (KBr): 2970, 1710, 1590 cm$^{-1}$.

$^1$H-NMR (CDCl$_3$): 1.1 (s, 1H), 1.45 (s, 2H), 1.25–2.0 (m, 8H), 2.1–3.2 (m, 4H), 2.5 (s, broad, 1H), 6.65–7.3 (m, 4H) ppm.

$^{13}$C-NMR (CDCl$_3$): 19.388, 20.054, 20.236, 20.599, 20.781, 22.901, 31.746, 32.413, 33.140, 33.624, 34.412, 44.529, 45.074, 46.952, 48.285, 50.950, 80.332, 80.514, 115.772, 116.620, 120.497, 120.982, 124.919, 126.010, 128.070, 128.554, 129.401, 208.157, 208.642 ppm.

EXAMPLE 20

According to general procedure AV-5, 3.3 g. cycloheptanone were reacted with 4-(2-hydroxyphenyl)-trans-3-buten-2-one. The residue was taken up in hot diisopropyl ether and the precipitate obtained after cooling was discarded. From the mother liquor, by crystallisation from diisopropyl ether, there was obtained 0.46 g. (6% of theory) B/C-cis-5,6-dihydro-2-methyl-2,11-cycloheptano-2,6-methano-1-benzoxocin-4(3H)-one; m.p. 129° C.

Analysis for $C_{17}H_{20}O_2$ (M.W. 256.3): calc.: C 79.60%; H 7.86%. found: 79.60% 7.93%.

Molecular weight 256 (ms).

$^1$H-NMR (CDCl$_3$): 1.3–2.1 (m, 10H), 2.2 (m, 2H), 2.6 (s, 2H), 2.7 (d, J=3 Hz, 1H), 3.1 (m, 1H), 6.7–7.2 (m, 4H).

From the mother liquor of the crystallisation, by crystallisation from methanol there was also isolated 0.46 g. (6% of theory) of the B/C-trans compound; m.p. 116° C.

EXAMPLE 21

According to general procedure AV-5, 3.0 g. 5,6-dihydro-2H-pyran-3(4H)-one were reacted with 4-(2-hydroxyphenyl)-trans-3-buten-2-one and the residue was separated on a Chromatron (elution agent petroleum ether/ethyl acetate 6:4 v/v). After recrystallisation from isopropanol, there was obtained 0.62 g. (8% of theory) B/C-trans-1H-3,4,4a,9a-tetrahydro-9a,10-propano-2,9-dioxaanthracen-12-one; m.p. 144° C.

Analysis for $C_{15}H_{16}O_3$ (M.W. 244.3): calc.: C 73.7%; H 6.60%. found: 73.6%; 6.66%.

Molecular weight 244 (ms).

IR (KBr): 2980, 1710, 1590 cm$^{-1}$.

$^1$H-NMR (CDCl$_3$): 1.6–2.3 (m, 4H), 2.35–2.7 (m, 2H), 2.85–3.4 (m, 3H), 3.4–3.8 (m, 2H), 3.9–4.3 (m, 1H), 6.67–7.3 (m, 4H) ppm.

$^{13}$C-NMR (CDCl$_3$): 26.566 (t), 36.502 (d), 37.501 (c), 43.467 (t), 46.467 (t), 68.095 (t), 74.153 (t), 76.000 (s), 116.741 (d), 120.891 (d), 125.858 (s), 128.494 (d), 128.585 (d), 151.454 (s), 207.764 (s) ppm.

EXAMPLE 22

According to general procedure AV-5, 3.5 g. 5,6-dihydro-2H-thiopyran-3(4H)-one were reacted with 4-(2-hydroxyphenyl)-trans-3-buten-2-one and the residue (2.8 g.) separated by chromatography (column chromatography, silica gel 60, elution agent petroleum ether/ethyl acetate 8:2 v/v). The following 4 fractions were obtained:

(a) B/C-trans-3H-1,2,4a,9a-tetrahydro-9a,10-propano-9-oxa-4-thiaanthracene-12-one, crystallised from isopropanol; m.p. 131° C.; yield 1.5 g. (19.5% of theory).

Analysis for $C_{15}H_{16}O_2S$ (M.W. 260.4): calc.: C 69.2%; H 6.20%; S 12.31%. found: 69.0%; 6.19%; 12.41%.

Molecular weight 260 (ms).

IR (KBr): 2940, 1710, 1590 cm$^{-1}$.

$^1$H-NMR (CDCl$_3$): 1.65–2.0 (m, 3H), 2.0–2.3 (m, 1.5H), 2.4–2.6 (m, 1.5H), 2.6–2.9 (m, 2.5H), 3.0–3.7 (m, 2.5H), 3.25 (m, 1H), 6.6–7.3 (m, 4H) ppm.

$^{13}$C-NMR (CDCl$_3$): 25.930 (t), 29.353 (t), 37.077 (d), 37.665 (t), 43.559 (d), 44.559 (t), 46.528 (t), 78.817 (s), 116.559 (d), 120.800 (d), 124.768 (s), 128.070 (d), 129.675 (d), 151.424 (s), 207.461 (s) ppm.

(b) B/C-cis-3H-1,2,4a,9a-tetrahydro-9a,10-propano-9-oxa-4-thiaanthracene-12-one, crystallised from ethyl acetate; m.p. 168° C.; yield 0.59 g. (7.4% of theory).

Analysis for $C_{15}H_{16}O_2S$ (M.W. 260.4): calc.: C 69.2%; H 6.20%; S 12.41%. found: 69.0%; 6.16%; 12.30%.

Molecular weight 260 (ms).

IR (KBr): 2950, 1710, 1590 cm$^{-1}$.

$^1$H-NMR (CDCl$_3$): 1.5–2.3 (m, 5H), 2.4–2.9 (m, 5H), 3.18 (q, J=3 Hz, 1H), 3.62 (d, J=2 Hz, 1H), 6.7–7.3 (m, 4H).

$^{13}$C-NMR (CDCl$_3$): 21.569 (t), 28.323 (t), 37.835 (t), 38.471 (d), 42.439 (d), 50.405 (t), 54.191 (t), 74.486 (s), 116.287 (d), 120.800 (d), 121.587 (s), 128.615 (d), 128.615 (d), 151.090 (s), 205.825 (s).

(c) B/C-trans-1H-3,4,4a,9a-tetrahydro-9a,10-propano-9-oxa-2-thiaanthracene-12-one, crystallised from isopropanol; m.p. 155° C.; yield 0.66 g. (8.5% of theory).

Analysis for $C_{15}H_{16}O_2S$ (M.W. 260.4): calc.: C 69.2%; H 6.20%; S 12.31%. found: 69.1%; 6.21%; 12.19%.

Molecular weight 260 (ms).

IR (KBr): 2960, 1700, 1590 cm$^{-1}$.

$^1$H-NMR (CDCl$_3$): 2.0–2.3 (m, 3H), 2.4–2.8 (m, 6H), 3.0 (m, 1H), 3.0 (d, J=18 Hz, 1H), 3.68 (d, J=18 Hz, 1H), 6.6–7.3 (m, 4H) ppm.

$^{13}$C-NMR (CDCl$_3$): 28.414 (t), 29.686 (t), 37.683 (d), 38.259 (t), 39.127 (d), 125.768 (s), 128.039 (d), 128.282 (d), 151.757 (s), 207.824 (s) ppm.

(d) B/C-cis-1H-3,4,4a,9a-tetrahydro-9a,10-propano-9-oxa-2-thiaanthracene-12-one, crystallised from ethyl acetate; m.p. 197° C.; yield 0.06 g. (0.8% of theory).

Analysis for $C_{15}H_{16}O_2S$ (M.W. 260.4): calc.: C 69.2%; H 6.20%; S 12.31%. found: 69.1%; 6.21%; 12.34%.

Molecular weight 260 (ms).

IR (KBr): 2960, 1710, 1590 cm$^{-1}$.

$^1$H-NMR (CDCl$_3$): 1.6–2.3 (m, 4H), 2.5–2.9 (m, 7H), 3.0 (m, 1H), 6.75–7.4 (m, 4H) ppm.

$^{13}$C-NMR (CDCl$_3$): 27.657 (t), 28.414 (t), 38.925 (t), 39.046 (d), 39.713 (d), 50.678 (t), 53.767 (t), 73.153 (s), 116.741 (d), 121.133 (d), 121.860 (s), 128.585 (d), 129.039 (d), 151.514 (s), 206.310 (s) ppm.

The same compound was also obtained when B/C-trans-1H-3,4,4a,9a-tetrahydro-9a,10-propano-9-oxa-2-thiaanthracene-12-one was treated in tetrahydrofuran with concentrated hydrochloric acid; yield 65% of theory.

EXAMPLE 23

0.52 g. (0.002 mole) B/C-trans-3H-1,2,4a,9a-tetrahydro-9a,10-propano-9-oxa-4-thiaanthracene-12-one was stirred with 1.6 ml. hydrogen peroxide and 1.9 ml. acetic acid for 30 minutes at 95° C. The resultant precipitate was recrystallised from ethyl acetate and 0.38 g. (65% of theory) B/C-trans-3H-1,2,4a,9a-tetrahydro-9a,10-propano-9-oxa-2-sulphonaanthracene-12-one was obtained.

Analysis for $C_{15}H_{16}O_4S$ (M.W. 292.4): calc.: C 61.1%; H 5.52%; S 10.97%. found: 61.5%; 5.62%; 10.86%.

Molecular weight 292 (ms).

IR (KBr): 2930, 1705, 1590 cm$^{-1}$.

$^1$H-NMR (CDCl$_3$): 1.7–2.5 (m, 6H), 2.65 (d, J=1.5 Hz, 1H), 3.0–3.35 (m, 2H), 3.4–3.85 (m, 2H), 4.1 (q, J=3 Hz, 1H), 6.7–7.3 (m, 4H) ppm.

EXAMPLE 24

3.9 g. (0.02 mole) 1,2,5,6-tetrahydro-1-acetyl-4-pyrrolidinopyridine and 5.0 g. (0.02 mole) 4-(2-methoxyethoxymethoxyphenyl)-trans-3-buten-2-one in 30 ml. toluene were heated under reflux for 24 hours under an atmosphere of nitrogen. Subsequently, 15 ml. of buffer solution (acetic acid/sodium acetate/water 1:1:2) were added thereto and heating continued for 4 hours. The toluene layer was separated off and washed with dilute hydrochloric acid, dilute aqueous sodium hydroxide solution and water. After drying, the solution was evaporated. After purification on a Chromatron (elution agent methylene chloride/ethyl acetate/isopropanol 20:80:5 v/v/v), there was obtained 0.55 g. (7.4% of theory) of a colourless liquid of 7H-1,2,3,4,8,8a-hexahydro-8-(2-methoxyethoxymethoxyphenyl)-6-oxoisoquinoline-2-acetamide.

1.5 g. (0.04 mole) of this acetamide in 20 ml. tetrahydrofuran was mixed with 20 ml. concentrated hydrochloric acid. After stirring for 4 days at ambient temperature, the reaction mixture was evaporated in a vacuum and the residue purified on a Chromatron (elution agent methylene chloride/ethyl acetate/isopropanol 20:80:5 v/v/v). From toluene/diisopropyl ether, there was obtained B/C-cis-1,4,4a,9a-tetrahydro-12-oxo-9a,10-propano-9-oxa-3-azaanthracene-3-acetamide in crystalline form; m.p. 175° C.; yield 0.64 g. (56% of theory).

Analysis for $C_{17}H_{19}NO_3$ (M.W. 285.3): calc.: C 71.6%; H 6.71%; N 4.91%. found: 71.6%; 6.73%; 4.83%.

Molecular weight 285 (ms).

IR (KBr): 2900, 1705, 1630, 1580 cm$^{-1}$.

$^1$H-NMR (CDCl$_3$): 1.65–2.1 (m, 3H), 2.2 (s, 3H), 2.3–2.8 (m, 5H), 3.0–3.3 (m, 2H), 3.5–3.7 (m, 1H), 4.3–4.8 (m, 1H), 6.7–7.3 (m, 4H).

$^{13}$C-NMR (CDCl$_3$): 21.205 (q), 35.926 (d), 37.622 (t), 38.228 (d), 41.681 (t), 42.227 (t), 50.344 (t), 53.071 (t), 75.001 (s), 116.499 (d), 121.587 (s), 121.587 (d), 128.797 (d), 129.039 (d), 151.211 (s), 170.294 (s), 206.098 (s).

F. Process for the Preparation of Ketones of General Formula (IV) From Enamines

General Procedure AV-6

I. 0.02 mole of freshly distilled enamine was heated under reflux for 24 hours, while gassing with nitrogen, with 0.02 mole freshly distilled enone of general formula (V) in 30 ml. toluene. 15 ml. buffer solution (acetic acid/sodium acetate/water 1:1:2 v/v/v) were then added thereto and the mixture was heated for 4 hours. The toluene layer was separated off, washed with dilute hydrochloric acid, dilute aqueous sodium hydroxide solution and water, then dried and evaporated in a rotary evaporator.

II. 0.004 mole of the compound thus obtained was dissolved in 20 ml. tetrahydrofuran and 10 ml. concentrated hydrochloric acid added dropwise thereto. Subsequently, the reaction mixture was stirred for 4 hours at ambient temperature and evaporated in a vacuum.

EXAMPLE 25

4-(2-Methoxyethoxymethoxyphenyl)-2,3,4,4a,5,6,7,8-octahydronaphthalene-2-one 3.0 g. (0.02 mole) pyrrolidinocyclohexane-(1) and 5.0 g. (0.02 mole) 4-(2-methoxyethoxymethoxyphenyl)-trans-3-buten-2-one were reacted according to general procedure AV-6 (I) and the residue was purified on a Chromatron (silica gel 60 PF 254, layer thickness 4 mm.; elution agent petroleum ether/ethyl acetate 8:2 v/v). There was obtained 1.9 g. (29% of theory) of a colourless liquid. The product was identified by thin layer chromatography (petroleum ether/ethyl acetate 8:2 v/v) and by NMR spectroscopy with reference to an authentic specimen.

EXAMPLE 26

B/C-trans-1,2,3,4,4a,9a-hexahydro-4a,9-propanoxanthen-12-one 1.32 g. (0.004 mole) of the compound of Example 25 was reacted according to general procedure AV-6 (II) and the residue recrystallised from methanol. Colourless needles were obtained in a yield of 0.85 g. (87.8% of theory); m.p. 141° C.

Analysis for $C_{16}H_{18}O_2$ (M.W. 242.3): calc.: C 79.3%; H 7.49%. found: 79.2%; 7.80%.

Molecular weight 242 (ms).

IR (KBr): 2970, 1710, 1590 cm$^{-1}$.

$^1$H-NMR (CDCl$_3$): 0.8–2.0 (m, 8H), 2.1 (m, 1H), 2.35–2.8 (m, 4H), 3.0 (m, 1H), 6.7–7.35 (m, 4H).

$^{13}$C-NMR (CDCl$_3$): 20.559 (t), 25.082 (t), 26.597 (t), 37.986 (t), 29.076 (d), 39.561 (d), 50.769 (t), 54.222 (t), 76.576 (s), 116.378 (d), 120.679 (d), 122.678 (s), 128.191 (d), 129.009 (d), 151.878 (s), 207.673 (s).

We claim:

1. 2,3,4,5,6,7-Hexahydro-2,7-methano-1,5-benzoxazonine and -1,4-benzoxazonine compounds, of the formula

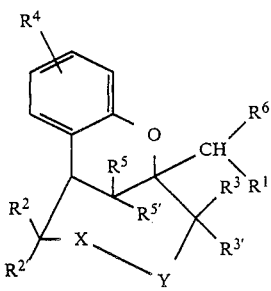

wherein:
R$_1$ is hydrogen or C$_1$–C$_4$ alkyl;
one of R$^2$ and R$^{2'}$ is hydrogen and the other is hydrogen or C$_1$–C$_4$ alkyl;
one of R$^3$ and R$^{3'}$ is hydrogen and the other is hydrogen, C$_1$–C$_4$ alkyl or phenyl;
R$^4$ is in the ortho- or para-position to the oxygen atom and is hydrogen, halogen, C$_1$ or C$_2$ alkoxy or C$_1$–C$_4$ alkyl;
each of R$^5$ and R$^{5'}$ is hydrogen or C$_1$–C$_4$ alkyl;
R$^6$ is hydrogen or C$_1$–C$_4$ alkyl; and one of X and Y is CH$_2$ and the other is the group NR$^7$ in which R$^7$ is hydrogen or C$_1$–C$_4$ alkyl; and a pharmaceutically acceptable acid addition salt thereof.

2. Compounds according to claim 1 in which
R$_1$ is hydrogen or C$_1$–C$_4$ alkyl, and
each of R$^5$ and R$^{5'}$ is hydrogen or C$_1$–C$_4$ alkyl.

3. Compounds according to claim 2 in which any C$_1$–C$_4$ alkyl groups are individually methyl, ethyl or isopropyl.

4. Compounds according to claim 3 in which any alkyl groups are methyl.

5. Compounds according to claim 1 in which X is NR$^7$ and Y is CH$_2$.

6. Compounds according to claim 2 of the formula

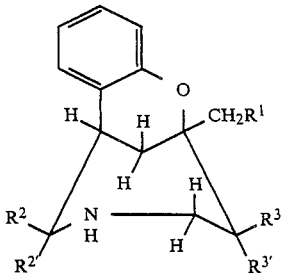

7. Compounds according to claim 6 in which any alkyl groups are methyl.

8. The compound of claim 7 which is 2,3,4,5,6,7-hexahydro-2-methyl-2,7-methano-1,5-benzoxazonine.

9. The compound of claim 7 which is 2,3,4,5,6,7-hexahydro-2,6-dimethyl-2,7-methano-1,5,-benzoxazonine.

10. an analgesic pharmaceutical composition comprising an effective amount of at least one pharmaceutically effective compound according to claim 1 in a pharmaceutically acceptable carrier or additive.

11. A composition according to claim 10 comprising a compound of the formula 2,3,4,5,6,7-hexahydro-2-methyl-2,7-methano-1,5-benzoxazonine or 2,3,4,5,6,7-hexahydro-2,6-dimethyl-2,7-methano-1,5-benzoxazonine.

12. A method for treating humans or animals which comprises administering thereto a pharmaceutically effective amount of a compound according to claim 1 for use as an analgesic.

13. A method for treating humans or animals which comprises administering thereto as an analgesic a pharmaceutically effective amount of a compound of the formula

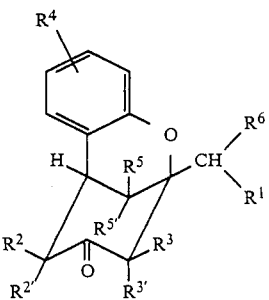

wherein:
R$_1$ is hydrogen or C$_1$–C$_4$ alkyl;
one of R$^2$ and R$^{2'}$ is hydrogen and the other is hydrogen or C$_1$–C$_4$ alkyl;
one of R$^3$ and R$^{3'}$ is hydrogen and the other is hydrogen, C$_1$–C$_4$ alkyl or phenyl;
R$^4$ is in the ortho- or para-position to the oxygen atoms and is hydrogen, halogen, C$_1$ or C$_2$ alkoxy or C$_1$–C$_4$ alkyl;
each of R$^5$ and R$^{5'}$ is hydrogen or C$_1$–C$_4$ alkyl;
and R$^6$ is hydrogen or C$_1$–C$_4$ alkyl.

14. A compound according to claim 2 wherein, R$^1$, R$^{2'}$, R$^3$, R$^{3'}$, R$^5$ and R$^{5'}$ are hydrogen; and R$^6$ is hydrogen or C$_1$–C$_4$ alkyl.

15. Compounds of the formula

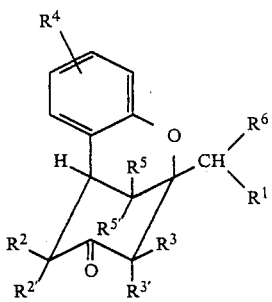

wherein:
R$_1$ is hydrogen or C$_1$–C$_4$ alkyl;
one of R$^2$ and R$^{2'}$ is hydrogen and the other is hydrogen or C$_1$–C$_4$ alkyl;
one of R$^3$ and R$^{3'}$ is hydrogen and the other is hydrogen, C$_1$–C$_4$ alkyl or phenyl;
R$^4$ is in the ortho- or para-position to the oxygen atom and is hydrogen, halogen, C$_1$ or C$_2$ alkoxy or C$_1$–C$_4$ alkyl;
R$^6$ is hydrogen or C$_1$–C$_4$ alkyl.

* * * * *

UNITED STATES PATENT AND TRADEMARK OFFICE
CERTIFICATE OF CORRECTION

PATENT NO. : 4,859,664
DATED : August 22, 1989
INVENTOR(S) : Friedrich Eiden, et al.

It is certified that error appears in the above-identified patent and that said Letters Patent is hereby corrected as shown below:

Col. 3, lines 21 & 23: change "2,7-methanol" to -- 2,7-methano --.

Col. 9, line 6: change "and is in" to -- and cis in --.

Col. 13, line 35: change "togeth4er" to -- together --.

Col. 24, line 7: change "6.67-7.3 (m, 4H)ppm" to -- 6.6-7.3 (m, 4H)ppm --.

Col. 26, line 62: change "29.076 (d)" to -- 39.076 (d) --.

Col. 27, line 59 (claim 10, line 1): change "an" to -- An --.

Signed and Sealed this

Twenty-third Day of October, 1990

Attest:

HARRY F. MANBECK, JR.

*Attesting Officer*  *Commissioner of Patents and Trademarks*